United States Patent [19]

Moen et al.

[11] Patent Number: 5,502,041
[45] Date of Patent: Mar. 26, 1996

[54] POTENT INHIBITOR OF HIV REVERSE TRANSCRIPTASE

[75] Inventors: Laura K. Moen, Norfolk; Gary F. Clark, Chesapeake, both of Va.

[73] Assignee: The Center for Innovative Technology, Herndon, Va.

[21] Appl. No.: 989,114

[22] Filed: Dec. 11, 1992

[51] Int. Cl.$^6$ .......................... A61K 31/715; C08B 31/00
[52] U.S. Cl. .............................. 514/54; 536/45; 514/934; 435/184; 435/194
[58] Field of Search ................................ 514/54; 536/45; 435/184, 194

[56] References Cited

PUBLICATIONS

Chem. Abst. 113 (15): 126079c, 1990.
Chem. Abst. 116 (3): 15396w, 1992.
Chem. Abst. 116 (15): 143361t, 1992.

*Primary Examiner*—John W. Rollins
*Attorney, Agent, or Firm*—Whitham, Curtis, Whitham & McGinn

[57] ABSTRACT

An isolated, substantially pure, novel compound possessing HIV reverse transcriptase inhibitory activity, and method of preparing same are described.

3 Claims, 7 Drawing Sheets

POTENT INHIBITOR OF HIV REVERSE TRANSCRIPTASE

The present invention is related generally to reverse transcriptase (RT) inhibitors. More particularly, the present invention is related to the isolation of a substantially pure inhibitor of human immunodeficiency virus (HIV) reverse transcriptase from fucoidan.

Retroviruses are single-stranded viruses which replicate by reverse transcription of the single-stranded RNA to ultimately yield a double-stranded DNA copy of the viral genome. This double-stranded DNA is then integrated into the host's genetic information to form the provirus. The enzyme responsible for converting the single-stranded RNA to double-stranded DNA is an RNA-directed DNA polymerase. These polymerases, also known as reverse transcriptases, are viral proteins which are required for viral replication to occur. Since the provirus cannot be formed without the reverse trancriptase activity, these enzymes are putative chemotherapeutic targets for retroviral-induced diseases, including AIDS and cancer.

The discovery that AIDS is caused by HIV, a retrovirus, has spawned great interest in antiretroviral agents. However, two of such currently approved therapeutic agents are both nucleoside analogs, and both have significant toxicities when used over extended periods. Hence, development of other classes of effective antiretroviral agents is of paramount importance.

The polysaccharides represent a class of compounds currently being explored for potential chemotherapeutic use against retroviral diseases. The polysaccharides isolated from marine algae are particularly promising, and some have been demonstrated to inhibit viral growth. Fucoidan, isolated from the brown algae *Fucus vesiculosus*, is one of these polysaccharides (Sugawa et al, 1989, Experientia, 45:996–998). However, fucoidan and the polysaccharides from other marine organisms are not simple compounds; they are complex mixtures of many carbohydrate structures. At present, neither the mechanism nor the nature of the RT inhibitory component of fucoidan is known or characterized.

SUMMARY OF INVENTION

It is, therefore, an object of the present invention to provide a substantially pure HIV RT inhibiting component isolated from a crude preparation of fucoidan.

It is a further object of the present invention to provide a new method of inhibiting HIV RT activity.

Other objects and advantages will become evident from the following detailed description of the invention.

BRIEF DESCRIPTION OF DRAWINGS

The foregoing and other objects, features and many of the attendant advantages of the invention will be better understood upon a reading of the following detailed description when considered in connection with the accompanying drawings, wherein.

DETAILED DESCRIPTION OF THE INVENTION

The above and various other objects and advantages of the present invention are achieved by an isolated, substantially homogeneous, brown pigmented compound, soluble in aqueous medium (e.g. buffers, etc.), having the following properties:

(a) being inhibitory to HIV RT activity;

(b) having a molecular weight of approximately 12 kD as determined by BioGel P10 chromatography.

Figure 4:
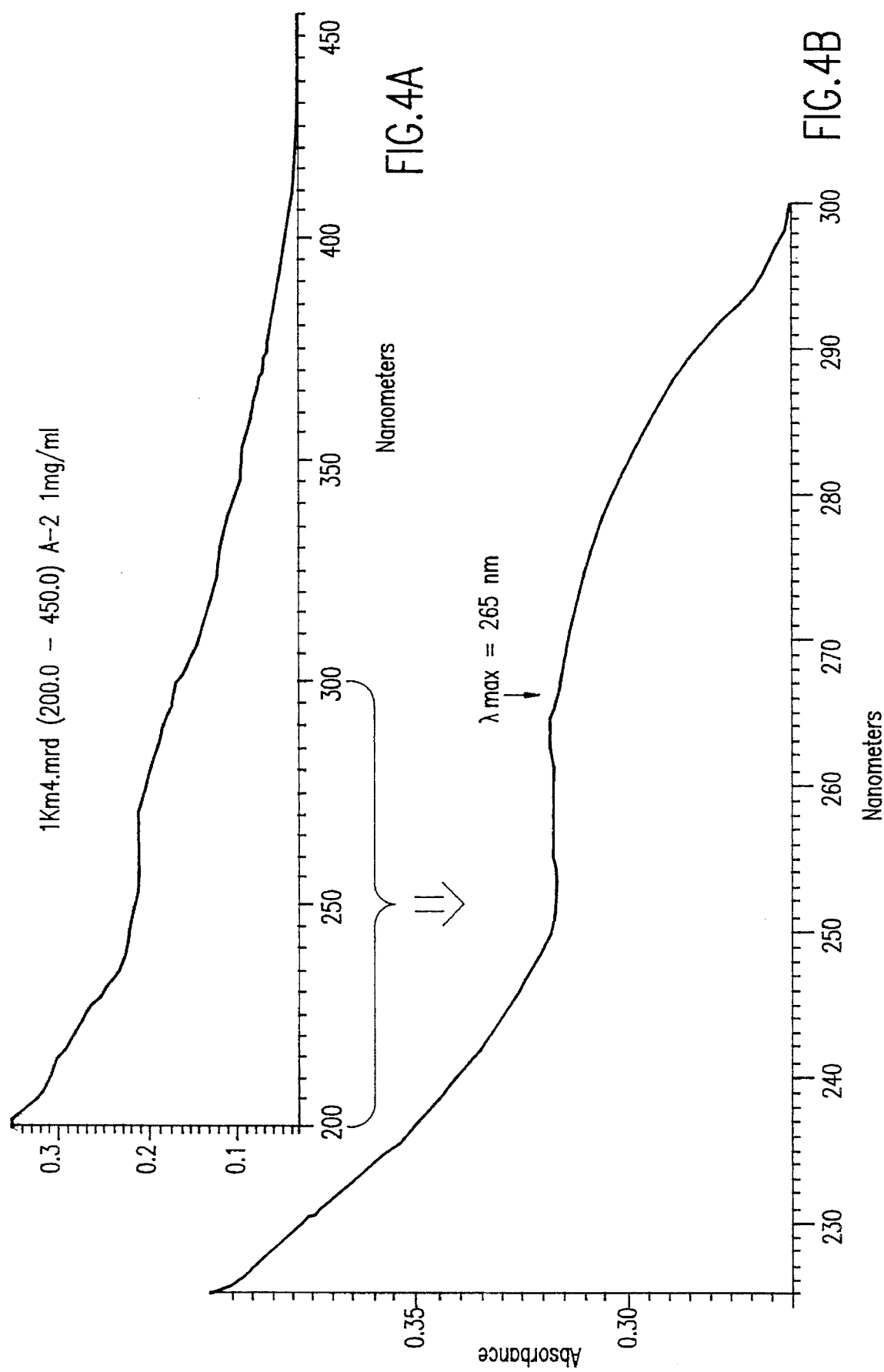
FIG. 4 is an ultraviolet-visible (UV-Vis) scan of the purified HIV RT inhibitor component of the present invention.
Figure 7:
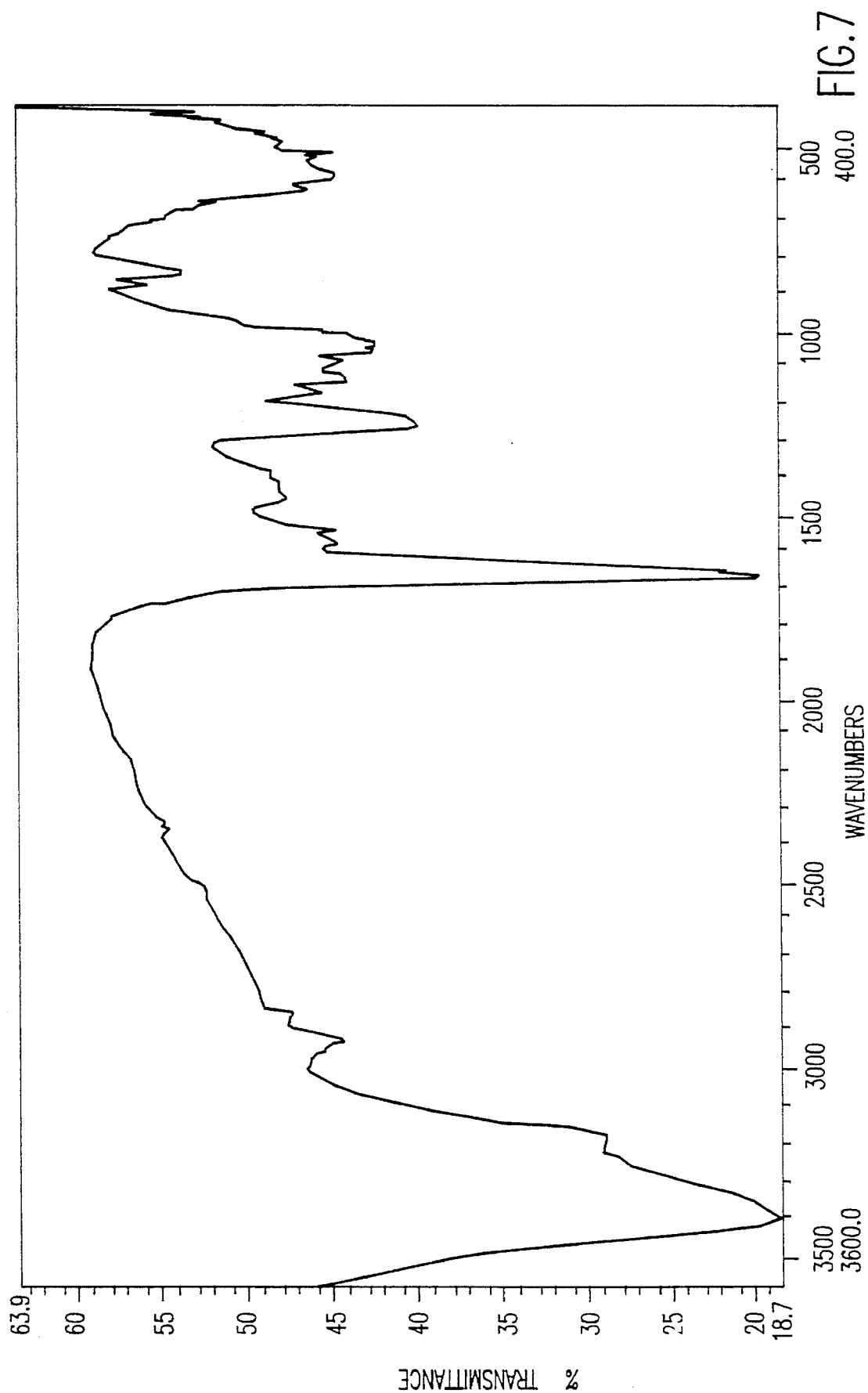
FIGS. 7 and 8 show an infrared and NMR spectra, respectively, of the compound of the present invention.
Figure 8:
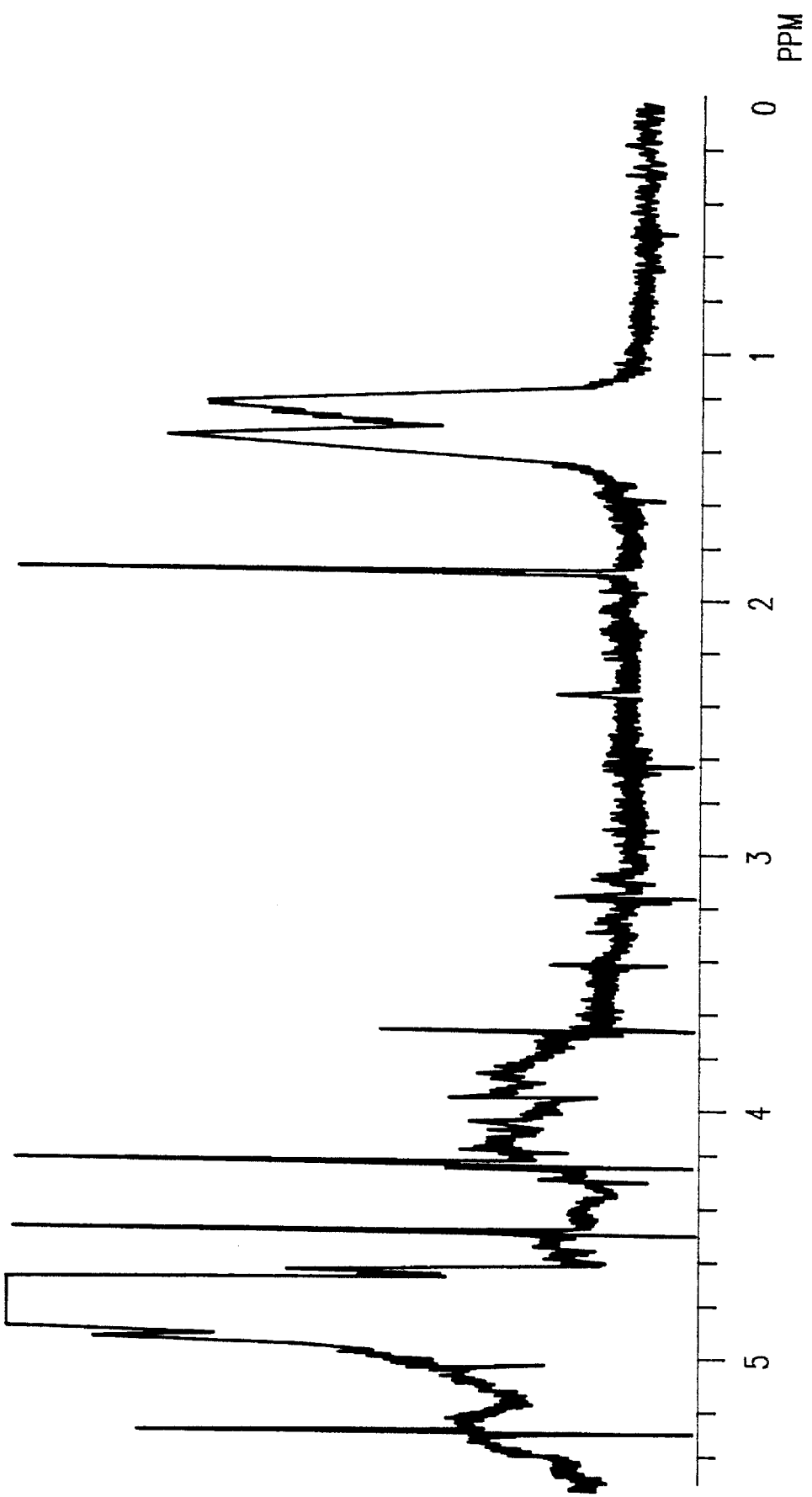

(c) having an ultraviolet absorption spectrum as shown in FIG. 4;

(d) lacking polysaccharide structure;

(e) being non-competitive with dTTP;

(f) being insoluble in organic solvents;

(g) having an infrared spectrum as shown in FIG. 7;

(H) having an NMR spectrum as shown in FIG. 8; and (i) being composed of at least the following elements (% weight): C: 20.52 (±0.5%); H: 4.64 (±0.4%); N: 20.38 (±0.6%) and O: 36.19 (±1%).

Unless defined otherwise, all technical and scientific terms used herein have the same meaning as commonly understood by one of ordinary skill in the art to which the invention belongs. Although any methods and materials similar or equivalent to those described herein can be used in the practice or testing of the present invention, the methods and materials described herein are preferred. Unless mentioned otherwise, the techniques employed or contemplated are standard methodologies well known to the skilled artisan. The materials, methods and examples are only illustrative and not limiting.

The term "substantially pure" as used herein means the compound is purified to homogeneity and is as pure as can be obtained by standard or conventional purification techniques currently available.

MATERIALS AND METHODS

Crude Fucoidan Preparation

Crude fucoidan preparation was obtained from Sigma Chemicals, St. Louis, Mo. (Cat. #F5631).

HIV RT Preparation and Assay

HIV RT purification is an established procedure (Bathurst et al, 1990, Biochem. Biophys. Acta, 171:589–595) and so are the assays for HIV RT activity (Moen et al, 1991, AIDS Research and Human Retroviruses, 8:597–604).

Briefly, the HIV RT assay was performed by determining the incorporation of radioactive nucleotide into acid-precipitable nucleic acid as described by Cheng et al, 1987, J. Biol. Chem. 262:2187–2189, but with a few modifications. 50 mM Tris, pH 8.5, 0.1% Triton X-100, 10 mM $MgCl_2$, 60 mM KCl, 2 µg primer-template and 40 µM dTTP (deoxythymidine triphosphate) were loaded into a 1.5 ml Eppendorf tube in a total volume of 40 µl. Specific activity of [$^3$H]-dTTP was 0.25 µCi/nmol dTTP. In the case of inhibition assays, the reaction mix for each inhibition included the appropriate amount of inhibitor. Reactions were initiated with 10 µl of diluted enzyme and incubated at 37 C. for 30 minutes. The reactions were quenched with 1 ml ice-cold 10% TCA (trichloroacetic acid) containing 10 mM PPi (pyrophosphate) and maintained at 0 C. until precipitated material was collected on Whatman GF/C filters. Each filter was washed three times with 2 ml of cold TCA solution and then rinsed with 1–2 ml ethanol. The dry filters were counted in 5 ml of scintillation cocktail in a Beckman Liquid Scintillation Counter.

Fractionation of Crude Fucoidan

Figure 1A:
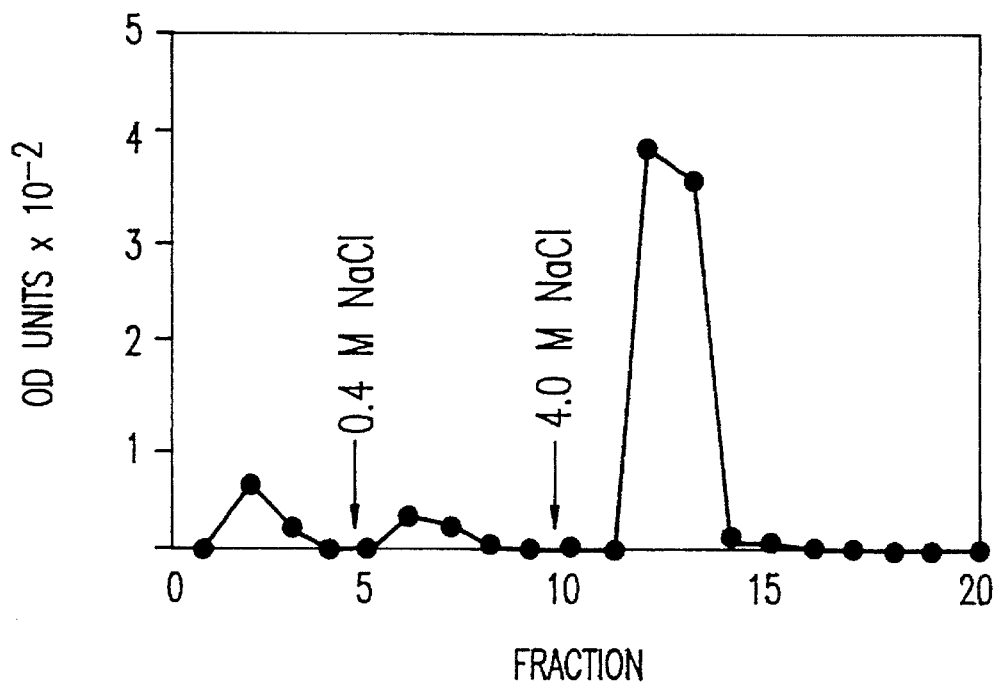
FIG. 1 shows the results of anion exchange chromatography of fucoidan inhibitor. Panel A: Fucoidan was dissolved in 2 mM Tris and applied to a column of QAE-Sepharose (1×20 cm) equilibrated in the same buffer. 2.5 ml fractions were collected and assayed for hexose using the standard phenol-sulfuric acid assay. One O.D. unit equals approximately 33 µg hexose. Panel B: The three fractions separated by ion exchange chromatography were pooled, desalted, and assayed for their inhibition of HIV RT activity: Neutral (N), moderately anionic (A), and highly anionic (HA).
Figure 1B:
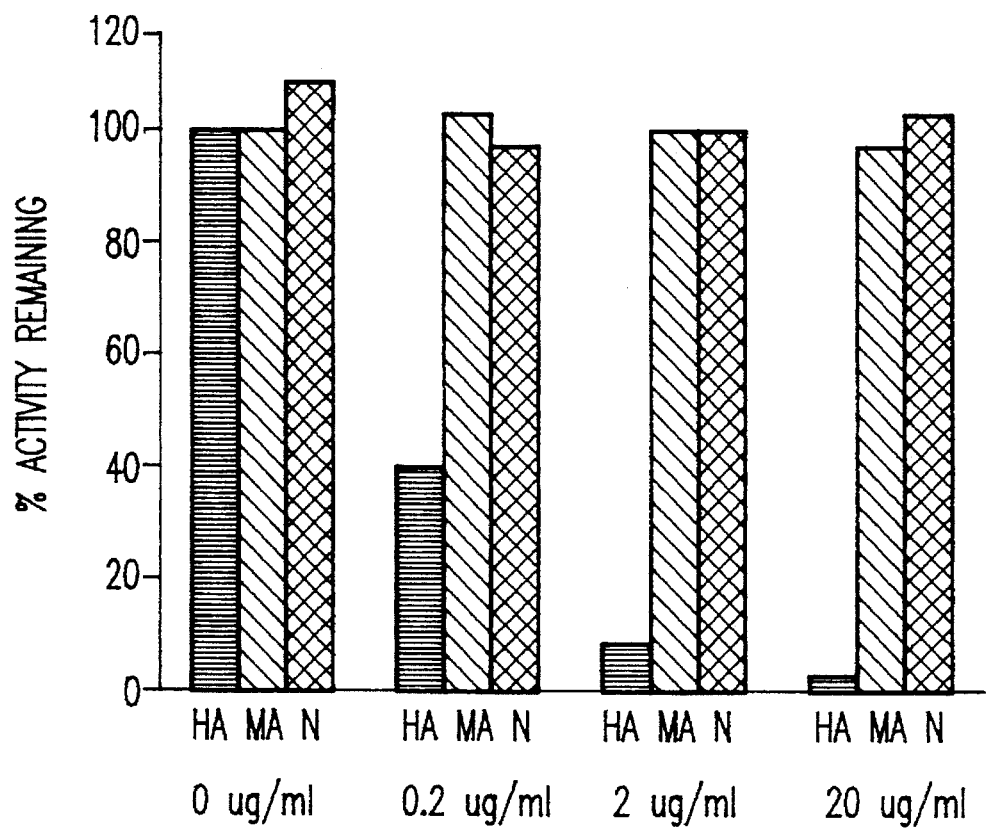

Since fucoidan is composed primarily of fucose sulfate, crude fucoidan was initially fractionated on a column of QAE-Sepharose as shown in FIG. 1. About 15% of the carbohydrate eluted without retention. About 5% was eluted with 0.4M NaCl-buffer solution. The remainder of the fraction (80%) was eluted with buffer containing 4M NaCl. Analysis of the three fractions indicated that all of the RT inhibitory activity resided in the highly anionic fraction. The neutral fraction eluted with 0.4M NaCl had no inhibitory activity at all in the RT assays (FIG. 1, Panel B). It was noted at this point that the highly anionic fraction contained a dark brown pigment that was absent in the other fractions.

Another method for isolating the HIV RT inhibitor of the present invention from crude fucoidan is as follows. The contents of a 5 g bottle of crude fucoidan is solubilized in 25 ml of Milli Q $H_2O$ and loaded onto a Dowex AG-1-X2 (Analytical grade, BioRad) acetate form resin which is packed as a 4.5×1 cm column in $H_2O$. The column is washed with 10 ml of water, followed by 10 ml of 1M NaOH. The eluant becomes basic at this point and any carbohydrate which remained on the column is eluted in this step (eluant appears golden brown). The column is washed again with water until the pH returns to neutral. The brown band at the top of the column is now eluted with 6N guanidine-HCl (molecular biology grade, Sigma). A dark, rich brown colored material (the compound of the present invention) elutes immediately. This eluant is concentrated by drying down to a small volume and resuspended in a small volume of water. It is then desalted on Biogel P10 or P6 and the desalted material used for testing of HIV RT activity or for other tests.

Figure 2:
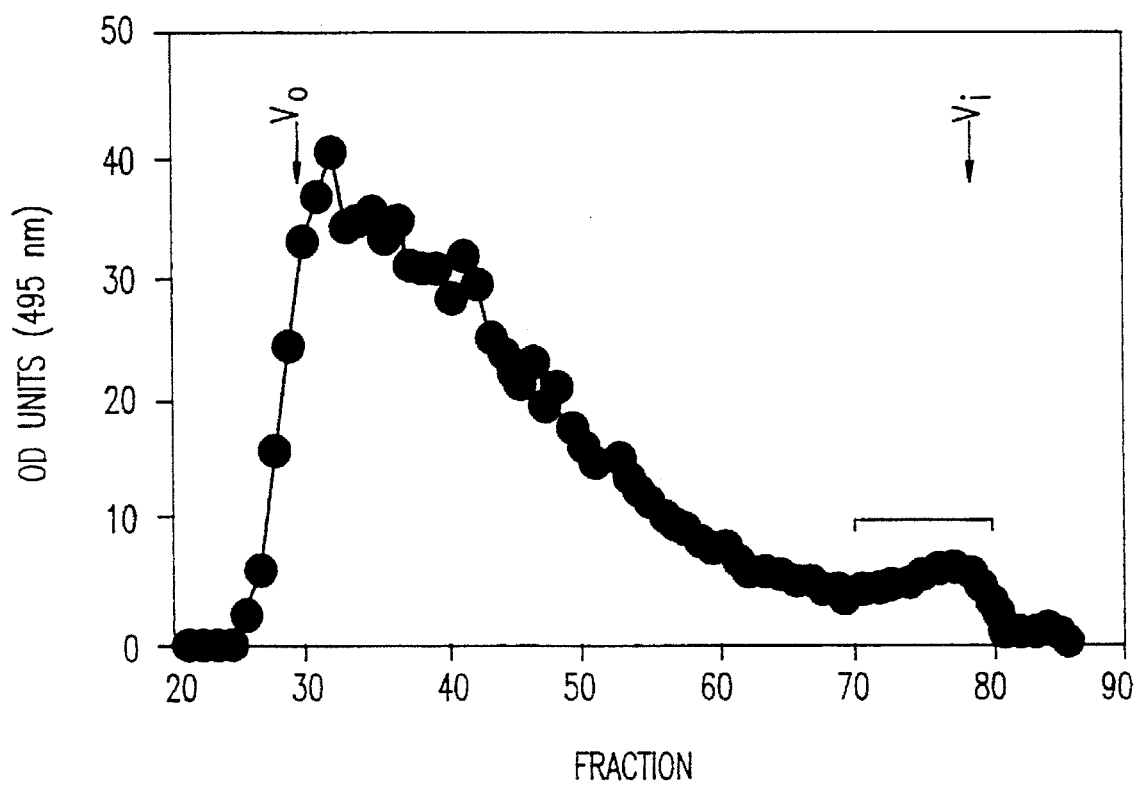
FIG. 2 shows the results of gel filtration analysis of fucoidan. Crude fucoidan was applied to a column (1×90 cm) of Sephadex G-200 (MW cutoff 250 kD). The buffer used for elution was 0.1M pyridine acetate, pH 5.4. Total hexose was detected as in FIG. 1. $V_0$ is the position of elution of dextran and $V_1$ is the position of elution of [$^3$H]galactose. The fraction size was 1 ml.

Evidence clearly indicating that the pigmented fraction was the active HIV RT inhibitor was obtained by gel filtration analysis. Crude fucoidan was separated on a column of Sephadex G-200 into high, medium and lower molecular weight fractions (FIG. 2). Only the lower molecular weight fractions (shown in brackets) had any inhibitory activity; the other fractions were not active at all as inhibitors. Again, the pigmented component eluted at precisely the same position where the inhibitor activity was found. When the highly anionic fraction was separated on this column, nearly all of the carbohydrate eluted near the void volume of the column whereas the pigmented compound eluted near the included volume of the column. These results, together with the results shown in FIG. 1, clearly established that the pigmented component possessing the HIV RT inhibitory activity was not a carbohydrate.

Figure 3:
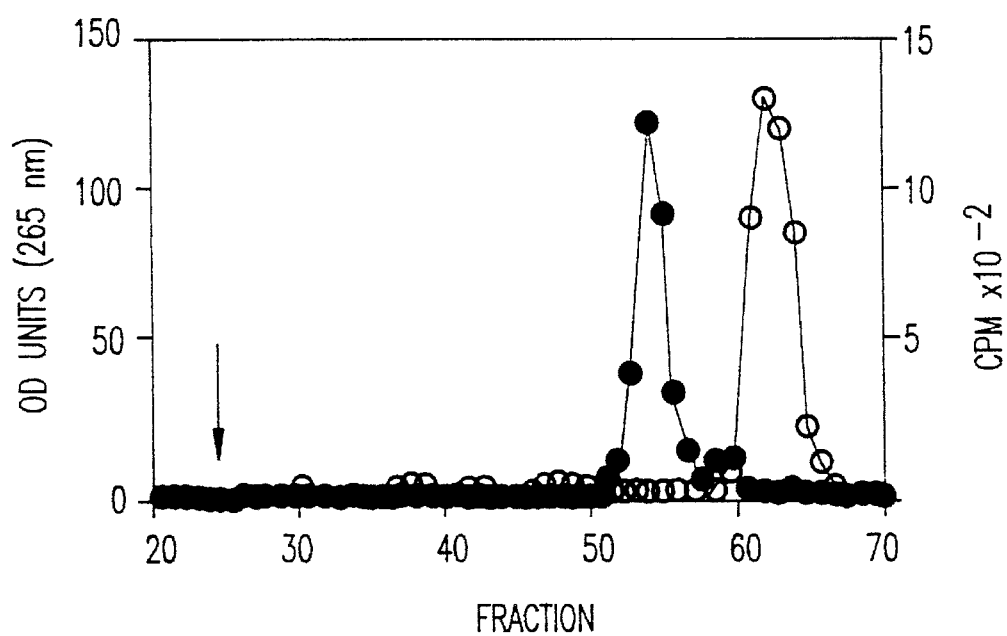
FIG. 3 shows the separation of purified RT inhibitor by gel permeation chromatography. Semipurified inhibitor was diluted with [$^3$H]galactose and fractionated on a column (2.5×45 cm) of BioGel P10 (400 mesh) equilibrated in 0.1M pyridine acetate, pH 5.4. Fractions (2.5 ml) were collected, dried on a speed-vac apparatus, and suspended in deionized distilled water. The inhibitor (closed circles) was followed by its absorbance at 265 nm. [$^3$H]galactose (open circles) was detected by liquid scintillation counting. The position of elution of dextran (500 kD) is indicated by arrow.

Since this pigmented inhibitor is smaller than the fucans in this preparation, it was purified by a combination of dialysis and gel filtration. The inhibitor was dialyzed at 4 C. through cellulose membranes (MW cutoff 12–14 kD) against deionized water for 2–3 days. (The pigment will also pass through 6–8 kD W cutoff tubing, but more slowly). Only about 5–10% of the carbohydrate chains dialyze through the membrane but 90% of the pigmented compound passes through, based on its specific absorbance at 265 nm. The fraction was dried under vacuum and applied to a column of BioGel P10 (minus 400 mesh). The inhibitor was specifically detected by its absorbance at 265 nm. If complete purification is not obtained, the chromatography is repeated 2–3 times or until substantially pure (homogeneous) preparation is obtained. A typical final profile is shown in FIG. 3. The compound is detected as a narrow peak eluting just before [$^3$H]galactose. This purified fraction, devoid of carbohydrate is a dark brown substance that has an oiliness to it when hydrated. It forms dark crystals when lyophilized and is negative when tested for hexose, hexosamines, uronic acid or sulfate groups. Its apparent molecular weight as determined herein is about 12 kD. It is noted that if the pigmented inhibitor had hydrophobic properties, different M.W. would be obtained upon gel permeation chromatography using different media.

Spectroscopic Characterization

A UV-Vis scan of the purified compound is shown in FIG. 4. The most important characteristic to note on this scan are the two peaks with approximate absorption maxima at 210 and 265 nm. No absorbance was detected beyond 450 nm. These peaks, particularly that at 265 nm is one of the physical characteristics of the purified HIV RT inhibitory compound. Additional characteristics are defined by the infrared and NMR spectra shown in FIGS. 7 and 8, respectively.

Relationship to Other Alagal Pigments

Other pigments from marine algae include phyto pigments and fucoxanthin. Phyto pigments are related to heme and chlorophyll, and they do not have spectra such as those seen in FIG. 4. Fucoxanthin, as described in the Merck Index, is a carotenoid pigment. It is the major pigment found in *Fucus vesiculosus*, the source of crude fucoidan. However, fucoxanthins are soluble in organic solvents, such as acetone, ethanol, petroleum ether and the like, and have three absorption maxima at 292, 350 and 450 nm. Carotenoids, including fucoxanthin, are soluble in hexane which is primarily used for the extraction and isolation of carotenoid compounds. These compounds are not soluble in aqueous media. In contrast, the inhibitor of the present invention does not have the characteristic absorption maxima reported for fucoxanthin or other carotenoid pigments. Furthermore, this inhibitor is not soluble in organic solvents such as ethanol, methanol, benzene, acetone, $CHCl_3$, and the like, and it is particularly insoluble in hexane. However, it is soluble in water, aqueous buffers such as phosphate buffers, pyridine acetate buffers and the inclusion of detergents such as β-octylglucoside and the like increases its solubility. Fucoxanthin could not be detected in the compound of the present invention either by the organic extraction procedures or by thin layer chromatography (results not shown).

Type of Inhibition

Figure 5:
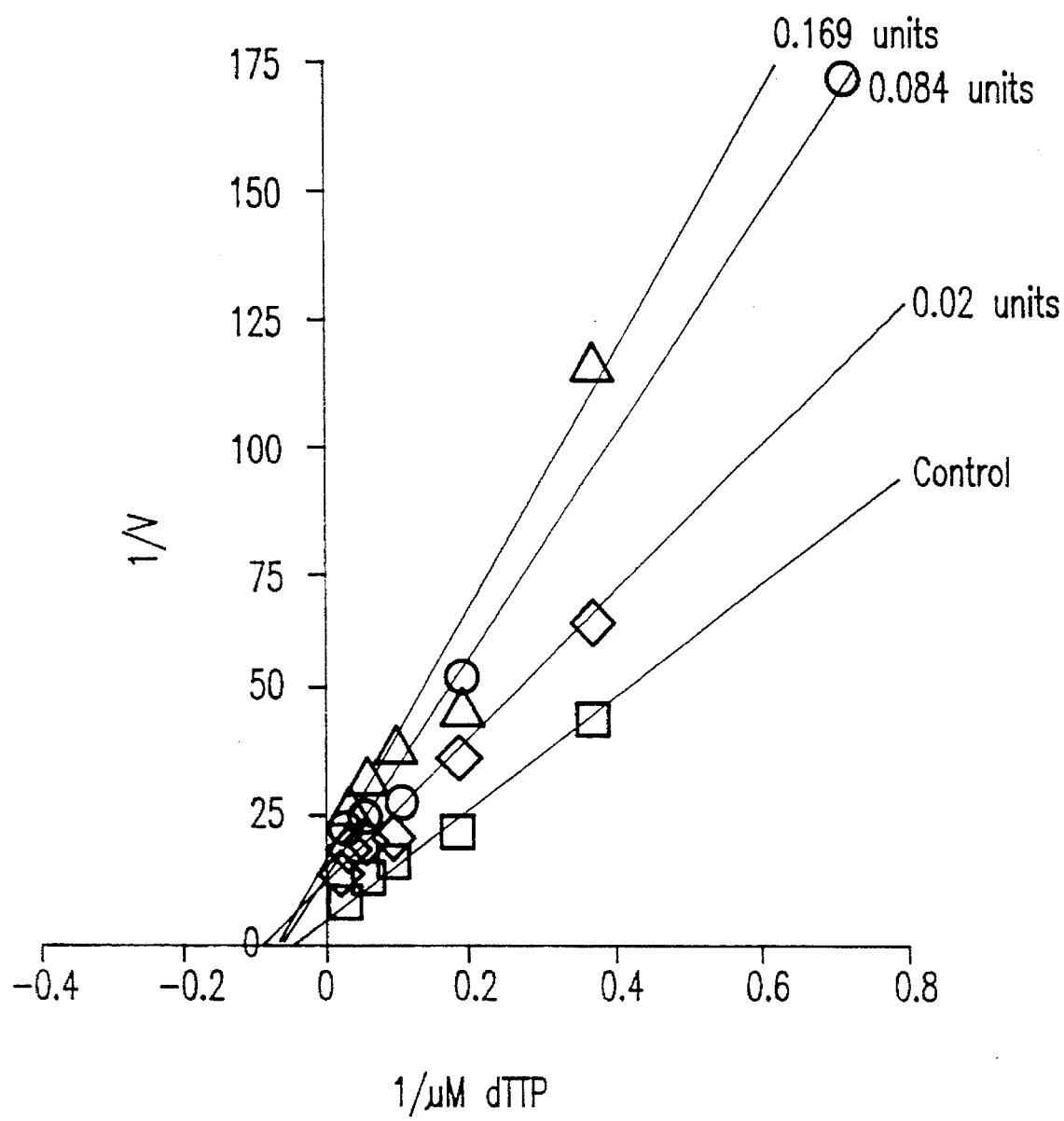
FIGS. 5 and 6 show the Lineweaver-Burke plots of inhibition studies performed with the compound of the present invention.

Kinetic studies were performed in order to determine the mechanism of inhibition. FIG. 5 shows a Lineweaver-Burke plot of inhibition studies run with different concentrations of the purified inhibitor of this invention and varied concentrations of dTTP, the nucleoside substrate. Primer-template (the nucleic acid substrate) was held constant in the experiments. Notice the intersection of the lines on the X-axis to the left of the origin. This pattern of intersecting lines is characteristic of noncompetitive inhibition; i.e., the inhibitor is not competing for the dTTP binding site. This result indicates that the inhibitor is neither a nucleotide nor a nucleotide antagonist, such as AZT or ddC or ddI, current drugs in clinical use.

Figure 6:
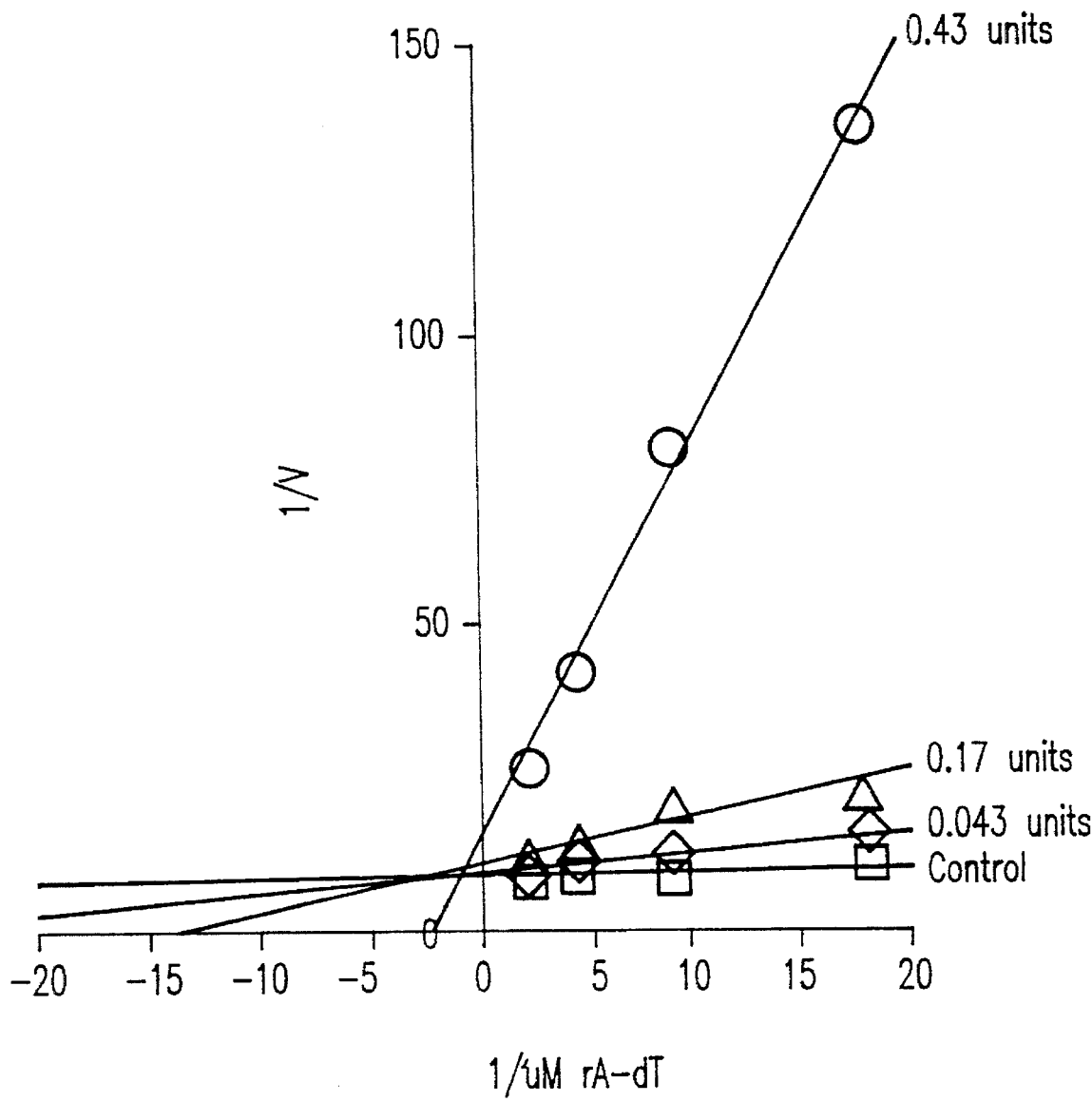

Further studies were performed as shown in the Lineweaver-Burke plot (FIG. 6). These inhibition studies were run with different concentrations of the inhibitor and varied concentrations of the primer-template. The concentration of dTTP was held constant at saturation in these experiments. Notice the intersection of the lines on or near the Y-axis above the origin. This pattern of intersecting lines is characteristic of competitive inhibition. The results indicate that the inhibitor of the present invention interferes with the ability of HIV RT to bind its nucleic acid substrate.

Inhibitor Is Not a Polysaccharide

Several inhibitors of HIV and HIV RT have been reported which are derived from marine sources. These inhibitors include alkaloids isolated from sponges and tunicates and various polysaccharides. Crude fucoidan is one such inhibitor, and the reported activity against HIV RT is thought to be a result of the polysaccharide component (Nakshima et al, 1987, Antimicrobial Agents Chemother. 31:1524–1528). However, as shown herein, the inhibitor material of the present invention is not a polysaccharide and represents a novel compound isolated from crude fucoidan. The inhibitor elutes as a discreet fraction in gel permeation chromatography and is negative when tested for hexose, hexosamines, uronic acid or sulfate groups (data not shown). Inhibition studies showed that the carbohydrate fraction removed during dialysis or gel filtration had little inhibitory activity or effect on the properties of the compound of the present invention.

It is understood that the examples and embodiments described herein are for illustrative purposes only and that various modifications or changes in light thereof will be suggested to persons skilled in the art and are to be included within the spirit and purview of this application and scope of the appended claims.

We claim:

1. An isolated, substantially pure compound isolated from fucoidan having the following properties:

(a) being brown pigmented;

(b) being insoluble in organic solvents;

(c) lacking hexose, hexosamine, uronic acid or sulfate groups;

(d) lacking polysaccharide structure;

(e) being inhibitory to HIV RT activity in vitro;

(f) being non-competitive with dTTP;

(g) having an ultraviolet absorption spectrum as shown in FIG. 4;

(h) having an apparent molecular weight of about 12 kD, as determined by gel chromotography;

(i) having an infrared spectrum as shown in FIG. 7;

(j) having an NMR spectrum as shown in FIG. 8;

(k) being composed of at least the following elements in % weight: C: 20.52 ($\pm$0.5%); H: 4.64 ($\pm$0.4%); N: 20.38 ($\pm$0.6%) and O: 36.19 ($\pm$1%); and (l) being soluble in aqueous medium.

2. A method of preparing a compound having HIV RT inhibitory activity in vitro, comprising the steps of:

(a) passing a crude preparation of fucoidan through an ion exchange material under conditions that allow said fucoidan preparation to be adsorbed on said ion exchange material; then (b) eluting a brown pigmented material possessing HIV RT inhibitory activity from said ion exchange material; then (c) purifying said pigmented material obtained in step (b) by standard purification techniques; and (d) obtaining a substantially pure preparation of a compound having HIV RT inhibitory activity in vitro.

3. A method inhibiting human immunodeficiency virus (HIV) reverse transcriptase (RT) activity in vitro, comprising the step of contacting HIV RT in vitro with sufficient amount of the compound of claim 1 to inhibit HIV RT activity in vitro.

\* \* \* \* \*